United States Patent [19]
Braswell et al.

[11] Patent Number: 5,972,895
[45] Date of Patent: Oct. 26, 1999

[54] COMPOSITION AND METHOD FOR INCREASING GROWTH HORMONE LEVELS

[75] Inventors: A. Glenn Braswell, Suite 420, 520 Washington Blvd., Marina Del Rey, Calif. 90292; Aftab J. Ahmed, Marina Del Rey, Calif.

[73] Assignee: A. Glenn Braswell, Atlanta, Ga.

[21] Appl. No.: 08/989,160

[22] Filed: Dec. 11, 1997

Related U.S. Application Data

[60] Provisional application No. 60/032,393, Dec. 11, 1996, abandoned.

[51] Int. Cl.$^6$ .................................................. A61K 38/08
[52] U.S. Cl. .......................................... 514/17; 530/329
[58] Field of Search .............................. 514/17; 530/329

[56] References Cited

U.S. PATENT DOCUMENTS

| | | | |
|---|---|---|---|
| 4,213,968 | 7/1980 | Kastin et al. | 514/17 |
| 4,223,019 | 9/1980 | Momany | 514/17 |
| 4,223,020 | 9/1980 | Momany | 514/17 |
| 4,223,021 | 9/1980 | Momany | 514/17 |
| 4,224,316 | 9/1980 | Momany | 514/17 |
| 4,226,857 | 10/1980 | Momany | 514/17 |
| 4,228,155 | 10/1980 | Momany | 514/17 |
| 4,228,156 | 10/1980 | Momany | 514/17 |
| 4,228,157 | 10/1980 | Momany | 514/17 |
| 4,228,158 | 10/1980 | Momany | 514/17 |
| 4,410,512 | 10/1983 | Bowers | 514/17 |
| 4,410,513 | 10/1983 | Momany . | |
| 4,411,890 | 10/1983 | Momany | 514/17 |
| 4,495,206 | 1/1985 | Wein | 426/250 |
| 4,497,800 | 2/1985 | Larson et al. | 514/2 |
| 4,512,923 | 4/1985 | Flegel et al. | 530/313 |
| 4,661,472 | 4/1987 | Rivier et al. | 514/15 |
| 4,725,577 | 2/1988 | Schally et al. | 514/11 |
| 4,839,344 | 6/1989 | Bowers et al. | 514/16 |
| 5,238,921 | 8/1993 | Maruyama et al. | 514/18 |
| 5,240,912 | 8/1993 | Todaro | 514/12 |
| 5,244,883 | 9/1993 | Cai et al. | 514/15 |
| 5,258,492 | 11/1993 | Schally et al. | 530/313 |
| 5,480,869 | 1/1996 | Wei et al. | 514/16 |
| 5,486,505 | 1/1996 | Bowers et al. | 514/16 |

OTHER PUBLICATIONS

Laron et al., "Intranasal Administration Of The GHRP Hexarelin Accelerates Growth In Short Children", Clinical Endocrinology, Nov. 1995, 43(5): 631–5 abst.

Massoud et al., "Hexarelin Induced Growth Hormone Release Is Influenced By Exogenous Growth Hormone", Clinical Endocrinology, Nov. 1995, 43(5): 617–21.

Roumi et al., "Radioimmunoassay For Hexarelin, A Peptidic Growth Hormone Secretagogue, And Its Phamaceutical Studies", Peptides, 1995, 16(7): 1301–6, abstract only.

Giustina et al., "Hexarelin, A Novel GHRP–6 Analog, Counteracts The Inhibitory Effect Of Hydrocortisone On Growth Hormone Secretion In Acromegaly", Endocrine Research, Aug. 1995, 21(3):569–82, abst.

Loche et al., "The Effect Of Hexarelin On Growth Hormone (GH) Secretion In Patients With GH Deficiency", Journal of Clinical Endocrinology and Metabolism, Sep. 1995, 80(9): 2692–6/ abst.

Matteini et al., "GH Secretion By Arginine Stimulus: The Effect of Both Low Doses and Oral Arginine Administered Before Standard Test", vol. LVI, 1980, pp. 2254–2261.

Ghigo et al., "Arginine Potentiates The GHRH—But Not The Pyridostigmine–Induced GH Secretion In Normal Short Children. Further Evidence for A Somastostatin Suppressing Effect of Arginine", Clinical Endocrinology (1990) vol. 32, 763–767.

Sato et al., "Mutual Priming Effects of GHRH and Arginine on GH Secretion: Informative Procedure for Evaluating GH Secretory Dynamics", Endocrinol. Japan. 1990, 37 (4) pp. 501–509.

Isidori et al., "A Study of Growth Hormone Release in Man After Oral Administration of Amino Acids", Current Medical Research and Opinion, vol. 7, No. 7, 1981, pp. 475–481.

Alba–Roth et al., "Arginine Stimulates Growth Hormone Secretion by Suppressing Endogenous Somatostatin Secretion", Journal of Clinical Endocrinology and Metabolism, vol. 67, No. 6, 1988, pp. 1186–1189.

McCann et al., "Gamma Amino Butyric Acid (GABA) Controls Anterior Pituitary Hormone Secretion", GABA and Endocrine Function, edited by Racagni et al., Raven Press, 1986, pp. 173–188.

Drugs, Review Article: Growth Harmone Secretagogous Zvi Laron, 50(4)595–601) 1995.

Molecular Biology of The Cell, 2nd Ed. Bruce et al., Garland Publishing, Inc. N.Y. pp. 55–56 and 58, 1989.

*Primary Examiner*—T. Moezie
*Attorney, Agent, or Firm*—Don J. Pelto; Lawrence M. Sung; Jeff E. Schwartz

[57] ABSTRACT

A composition for promoting the release and elevation of growth hormone levels includes (1) an oligopeptide of the formula A1-D2methylTrp-Ala-Trp-DPhe-Lys wherein A1 is glutamine (Gln) or glutamic acid (Glu), or (2) the oligopeptide in combination with free amino acids, particularly glutamine, glutamic acid, or a combination thereof, and organic or inorganic pharmaceutically acceptable salts thereof. The release and elevation of growth hormone levels may be promoted by administration of specified growth hormone releasing compounds.

24 Claims, No Drawings

COMPOSITION AND METHOD FOR INCREASING GROWTH HORMONE LEVELS

This nonprovisional application claims the benefit of U.S. Provisional Application No. 60/032,393, filed Dec. 11, 1996, now abandoned.

BACKGROUND OF THE INVENTION

1. Field of Invention

This invention relates to compounds which promote the release of growth hormone when administered to animals. In another aspect, this invention relates to methods for promoting the release and elevation of growth hormone levels in animals, including humans, by administration of specified growth hormone releasing compounds.

2. Description of Related Art

The elevation of growth hormone (GH) levels in mammals upon administration of GH-releasing compounds can lead to enhanced body weight and to enhanced milk production if sufficiently elevated GH levels occur upon administration. Further, it is known that the elevation of growth hormone levels in mammals can be accomplished by application of known growth hormone releasing agents, such as the naturally occurring growth hormone releasing hormones.

The elevation of growth hormone levels in mammals can also be accomplished by application of growth hormone releasing peptides, some of which have been previously described, for example, in U.S. Pat. No. 4,223,019, U.S. Pat. No. 4,223,020, U.S. Pat. No. 4,223,021, U.S. Pat. No. 4,224,316, U.S. Pat. No. 4,226,857, U.S. Pat. No. 4,228,155, U.S. Pat. No. 4,228,156, U.S. Pat. No. 4,228,157, U.S. Pat. No. 4,228,158, U.S. Pat. No. 4,410,512, U.S. Pat. No. 4,410,513, U.S. Pat. No. 4,411,890, U.S. Pat. No. 4,839,344, and U.S. Pat. No. 5,486,505.

Antibodies to the endogenous growth hormone release inhibitor somatostatin (SRIF) have also been used to cause elevated GH levels. In this latter example, growth hormone levels are elevated by removing the endogenous GH-release inhibitor (SRIF) before it reaches the pituitary, where it inhibits the release of GH.

Each of these methods for promoting the elevation of growth hormone levels involve materials which are expensive to synthesize and/or isolate in sufficient purity for administration to a target animal. Short chain, relatively simple peptides and free amino acids which have the ability to promote the release of growth hormone would be desirable because they could be readily and inexpensively prepared, easily modified chemically and/or physically, as well as easily purified and formulated; and they should have excellent transport properties.

It would be desirable to have short chain peptides and free amino acids which promote the release and elevation of growth hormone levels in the blood of animals, including humans. It would also be useful to be able to use such substances to promote the release and elevation of growth hormone levels in the blood of animals, including humans.

SUMMARY OF THE INVENTION

We have now discovered several novel compounds which promote the release of growth hormone in animals. The compounds comprise a novel oligopeptide, Brasium-2'2'2', a derivative of hexarelin, having the formula A1-D2methylTrp-Ala-Trp-DPhe-Lys, wherein A1 is glutamine (Gln) or glutamic acid (Glu), and the organic or inorganic pharmaceutically acceptable salts thereof. The oligopeptide may be used in conjunction with free amino acids which promote the release of growth hormone, in particular, glutamine or glutamic acid, or other growth hormone releasing stimulants.

Such compounds can be used to promote the release and elevation of blood growth hormone levels in animals, preferably humans, by administering an effective amount of the peptide.

DETAILED DESCRIPTION OF PREFERRED EMBODIMENTS

The present invention is based on the discovery of the promotion of the release and elevation of growth hormone levels in the blood of animals by a short chain peptide and free amino acids.

The amino acid residue abbreviations used herein are in accordance with the standard peptide nomenclature. All three letter amino acid abbreviations preceded by a "D" indicate the D-configuration of the amino acid residue.

Compounds of the present invention are easy and cost effective to synthesize, are effective in promoting an increase in serum growth hormone levels, and are desirable for commercial scale production and utilization. In addition, these compounds may be advantageous in having physiochemical properties which are desirable for the efficient delivery of such compounds to a wide variety of animal species.

The compounds comprise a novel oligopeptide, Brasium-2'2'2', a derivative of hexarelin, having the formula A1-D2methylTrp-Ala-Trp-DPhe-Lys, wherein A1 is glutamine (Gln) or glutamic acid (Glu), and the organic or inorganic pharmaceutically acceptable salts thereof. The oligopeptide may be used in conjunction with free amino acids which promote the release of growth hormone, in particular, glutamine, glutamic acid, arginine and lysine, or with other growth hormone releasing stimulants. These compounds have been shown to have a high level of potency in promoting the increase in serum growth hormone levels.

The compounds of this invention may be used to enhance blood GH levels in animals; enhance milk production in cows; enhance body growth in animals such as mammals (e.g., humans, sheep, bovines, and swine), as well as fish, fowl, other vertebrates and crustaceans; and increase wool and/or fur production in mammals. The amount of body growth is dependent upon the sex and age of the animal species, quantity and identity of the growth hormone releasing compound being administered, route of administration, and the like.

The novel oligopeptide of this invention can be synthesized according to the usual methods of solution and solid phase peptide chemistry, or by classical methods known in the art. The solid-phase synthesis is commenced from the C-terminal end of the peptide. A suitable starting material can be prepared, for instance, by attaching the required protected alpha-amino acid to a chloromethylated resin, a hydroxymethyl resin, a benzhydrylamine (BHA) resin, or a para-methyl-benzylhydrylamine (p-Me-BHA) resin. One such chloromethyl resin is sold under the tradename BIO-BEADS SX-1 by Bio Rad Laboratories, Richmond, Calif. The preparation of the hydroxymethyl resin is described by Bodansky et al., *Chem. Ind.* (London) 38, 1597 (1966). The BHA resin has been described by Pietta and Marshall, *Chem. Comm.*, 650 (1970) and is commercially available from Peninsula Laboratories, Inc., Belmont, Calif.

After the initial attachment, the alpha-amino protecting group can be removed by a choice of acidic reagents, including trifluoroacetic acid (TFA) or hydrochloric acid (HCl) solutions in organic solvents at room temperature. After removal of the alpha-amino protecting group, the remaining protected amino acids can be coupled stepwise in the desired order. Each protected amino acid can be generally reacted in about a 3-fold excess using an appropriate carboxyl group activator such as dicyclohexylcarbodiimide (DCC) or diisopropyl carbodiimide (DIC) in solution, for example, in methylene chloride (CH2Cl2) or dimethylformamide (DMF) and mixtures thereof.

After the desired amino acid sequence has been completed, the desired peptide can be cleaved from the resin support by treatment with a reagent such as hydrogen fluoride (HF), which not only cleaves the peptide from the resin, but also cleaves the most commonly used side-chain protecting groups. When a chloromethyl resin or hydroxymethyl resin is used, HF treatment results in the formation of the free peptide acid. When the BHA or p-Me-BHA resin is used, HF treatment results directly in free peptide amides.

The solid-phase procedure discussed above is well known in the art and has been described by Stewart and Young, *Solid Phase Peptide Synthesis: Second Edn.*, Pierce Chemical Co., Rockford, Ill. 1984.

Some solution methods which can be employed to synthesize the peptide moiety of the instant invention are set forth in Bodansky et al., *Peptide Synthesis*, 2nd Edition, John Wiley & Sons, New York, N.Y. 1976.

This preferred method of forming the oligopeptide is more fully described in WO 92/10709, by John C. Hubbs and S. W. Parker, entitled "Process for Synthesizing Peptides."

The free amino acids and other growth hormone releasing stimulants are readily available from numerous sources.

In accordance with another embodiment of the present invention, a method is provided for promoting release and/or elevation of growth hormone levels in the blood of an animal. The method comprises administering to an animal a dose of at least one of the above-described compounds, containing the oligopeptide or the oligopeptide and free amino acids or other growth hormone releasing stimulants, in an amount effective to promote the release of growth hormone.

The compounds of this invention can be administered by any suitable means known in the art, including oral administration, and can be formulated in dose forms appropriate for each route of administration. Oral administration is preferred.

Solid dose forms for oral administration include capsules, tablets, pills, powders and granules. In such solid dose forms, the active compound is mixed with at least one inert carrier such as sucrose, lactose, or starch. Such dose forms can also comprise, as is normal practice, additional substances other than inert diluents, e.g., lubricating agents such as magnesium stearate. In the case of capsules, tablets and pills, the dose forms may also comprise buffering agents. Tablets and pills can additionally be prepared with enteric coatings.

Liquid dose forms for oral administration include emulsions, solutions, suspensions, syrups, and elixirs containing inert diluents commonly used in the art, such as water. Besides such inert diluents, compositions can also include adjuvants, such as wetting agents, emulsifying and suspending agents, sweetening, flavoring, and perfuming agents.

The novel compounds of the present invention are also useful when administered in combination with growth hormone releasing hormone (i.e., naturally occurring growth hormone releasing hormone, analogs and functional equivalents thereof), as well as in combination with other compounds which promote the release of growth hormone, e.g., γ-Butyric Acid (GABA) or growth hormone releasing peptides (see U.S. Pat. Nos. 4,880,778 and 5,486,505, which are incorporated herein by reference). These growth hormone releasing stimulants may be used in an effective amount. For example, γ-Butyric Acid may be used in an amount of from about 0.70–4.0 mg per kilogram of body weight. It is preferred that γ-Butyric Acid be used in an amount of about 0.70 mg per kilogram of body weight.

The amount and composition of the compound of the present invention administered will vary depending on numerous factors, e.g., the particular animal treated, its age and sex, the desired therapeutic affect, and the route of administration. In all instances, however, a dose effective to promote release and elevation of growth hormone level in the blood of the recipient animal is used. The preferred amount can readily be determined empirically by the skilled artisan based upon the present disclosure.

For oral administration in humans, the dose level is typically about 0.10–0.25 mg/kg of body weight of the oligopeptide. Preferably, about 0.14 mg/kg of body weight of the oligopeptide is used. The exact level can readily be determined empirically based upon the present disclosure.

Free amino acids may also be used in the composition. About 0.70–7.0 mg per kilogram of body weight of an amino acid may be used. Preferably, 0.70 mg per kilogram of body weight is used. However, when the amino acid is glutamine or glutamic acid, about 7.0–30.0 mg per kilogram of body weight may be used. Preferably, 7.0 mg per kilogram of body weight is used.

In general, the administration of combinations of growth hormone releasing agents will allow for lower doses of the individual growth hormone releasing agents to be employed relative to the dose levels required for individual growth hormone releasing agents in order to obtain a similar response, due to the synergistic effect of the combination. Therefore, for example, per kilogram body weight, less amino acids are needed when administered in an embodiment of this invention then when administered alone.

Also included within the scope of the present invention are compositions comprising as an active ingredient the organic and inorganic addition salts of the above-described oligopeptide and combinations thereof, optionally in association with a carrier, diluent, slow release matrix, or coating.

The organic or inorganic addition salts of the growth hormone releasing peptide contemplated to be within the scope of the present invention include salts of such organic moieties as acetate, trifluoroacetate, oxalate, valerate, oleate, laurate, benzoate, lactate, tosylate, titrate, maleate, fumarate, succinate, tartrate, naphthalate, and the like; and such inorganic moieties as Group I (i.e., alkali metal salts), Group II (i.e. alkaline earth metal salts) ammonium and protamine salts, zinc, iron, and the like with counterions such as chloride, bromide, sulfate, phosphate and the like, as well as the organic moieties referred to above.

Pharmaceutically acceptable salts are preferred when administration to human subjects is contemplated. Such salts include the non-toxic alkali metal, alkaline earth metal and ammonium salts commonly used in the pharmaceutical industry including sodium, potassium, lithium, calcium, magnesium, barium, ammonium and protamine salts which are prepared by methods well known in the art. The term also includes non-toxic acid addition salts which are generally prepared by reacting the compounds of this invention with a suitable organic or inorganic acid. Representative salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napthylate, and the like.

The invention will be further illustrated by the following non-limiting example.

EXAMPLE

A composition of the following formulation was prepared in tablet form by standard methods:

| | |
|---|---|
| oligopeptide | 10 mg |
| Glutamine | 500 mg |
| L-Arginine | 50 mg |
| L-Lysine | 50 mg |
| γ-Butyric Acid (GABA) | 50 mg |
| Inert Diluent | as needed |

One tablet per day is the recommended dosage for an average weight adult human (70 kg).

The invention has been described in detail with particular reference to preferred embodiments thereof. However, it will be appreciated that those skilled in the art, upon consideration of this disclosure may make variations and modifications within the spirit and scope of the invention.

What is claimed is:

1. A peptide consisting of the formula A1-D2methylTrp-Ala-Trp-DPhe-Lys wherein A1 is glutamine (Gln) or glutamic acid (Glu), and organic or inorganic pharmaceutically acceptable salts thereof.

2. A method of promoting the release of growth hormone levels in an animal comprising administering to the animal a growth hormone release promoting effective amount of the peptide of claim 1.

3. The method of claim 2, wherein the animal is a human.

4. The method of claim 3, wherein the effective. amount of the peptide is from about 0.10–0.25 mg per kilogram of body weight.

5. The method of claim 4, wherein the effective amount of the peptide is 0.14 mg per kilogram of body weight.

6. A pharmaceutical composition for promoting the release of growth hormone levels in animals, comprising the peptide of claim 1 and a pharmaceutically acceptable carrier.

7. The pharmaceutical composition of claim 6, which further comprises free amino acids.

8. The pharmaceutical composition of claim 7, wherein the free amino acids are glutamine, glutamic acid, arginine, lysine, or a combination thereof.

9. The pharmaceutical composition of claim 6, wherein the peptide is present in an amount of from about 0.10–0.25 mg per kilogram of body weight.

10. The pharmaceutical composition of claim 9, wherein the peptide is present in an amount of 0.14 mg per kilogram of body weight.

11. The pharmaceutical composition of claim 8, wherein glutamine, glutamic acid, or a combination thereof are present in an amount of from about 7.0–30.0 mg per kilogram of body weight.

12. The pharmaceutical composition of claim 8, wherein arginine, lysine, or a combination thereof are present in an amount of from about 0.70–7.0 mg per kilogram of body weight.

13. The pharmaceutical composition of claim 11, wherein glutamine, glutamic acid, or a combination thereof are present in an amount of about 7.0 mg per kilogram of body weight.

14. The pharmaceutical composition of claim 12, wherein arginine, lysine, or a combination thereof are present in an amount of about 0.70 mg per kilogram of body weight.

15. The pharmaceutical composition of claim 6, further comprising a growth hormone releasing stimulant.

16. The pharmaceutical composition of claim 7, further comprising a growth hormone releasing stimulant.

17. A method of promoting the release of growth hormone levels in an animal comprising administering to the animal a growth hormone release promoting effective amount of the pharmaceutical composition of claim 6.

18. A method of promoting the release of growth hormone levels in an animal comprising administering to the animal a growth hormone release promoting effective amount of the pharmaceutical composition of claim 7.

19. A method of promoting the release of growth hormone levels in an animal comprising administering to the animal a growth hormone release promoting effective amount of the pharmaceutical composition of claim 15.

20. A method of promoting the release of growth hormone levels in an animal comprising administering to the animal a growth hormone release promoting effective amount of the pharmaceutical composition of claim 16.

21. The method of claim 17, wherein the animal is a human.

22. The method of claim 18, wherein the animal is a human.

23. The method of claim 19, wherein the animal is a human.

24. The method of claim 20, wherein the animal is a human.

* * * * *